United States Patent
Kamimoto et al.

(10) Patent No.: US 11,760,864 B2
(45) Date of Patent: Sep. 19, 2023

(54) TRISULFIDE COMPOUND

(71) Applicant: SUMITOMO CHEMICAL COMPANY, LIMITED, Tokyo (JP)

(72) Inventors: Natsuyo Kamimoto, Ichihara (JP); Takeshi Hara, Ichihara (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 106 days.

(21) Appl. No.: 17/608,465

(22) PCT Filed: Jun. 4, 2020

(86) PCT No.: PCT/JP2020/022037
§ 371 (c)(1),
(2) Date: Nov. 2, 2021

(87) PCT Pub. No.: WO2020/246527
PCT Pub. Date: Dec. 10, 2020

(65) Prior Publication Data
US 2022/0213295 A1    Jul. 7, 2022

(30) Foreign Application Priority Data

Jun. 7, 2019  (JP) .................................. 2019-107337

(51) Int. Cl.
| | | |
|---|---|---|
| *C08K 5/378* | (2006.01) | |
| *B60C 1/00* | (2006.01) | |
| *C07D 239/38* | (2006.01) | |
| *C08K 3/04* | (2006.01) | |
| *C08K 3/36* | (2006.01) | |
| *C08L 9/06* | (2006.01) | |

(52) U.S. Cl.
CPC ............... *C08K 5/378* (2013.01); *B60C 1/00* (2013.01); *C07D 239/38* (2013.01); *C08K 3/04* (2013.01); *C08K 3/36* (2013.01); *C08L 9/06* (2013.01)

(58) Field of Classification Search
CPC . B60C 1/00; C07D 239/38; C08L 9/06; C08L 9/00; C08L 91/00; C08K 3/36; C08K 3/04; C08K 3/30; C08K 5/378; C08K 5/31; C08K 5/47
See application file for complete search history.

(56) References Cited

U.S. PATENT DOCUMENTS

| | | | |
|---|---|---|---|
| 3,763,095 A | 10/1973 | Di Battista | |
| 4,837,322 A | 6/1989 | Deschler et al. | |
| 6,646,029 B1 | 11/2003 | Lin et al. | |
| 2010/0019203 A1* | 1/2010 | Akino | H05B 33/14 |
| | | | 252/301.35 |

FOREIGN PATENT DOCUMENTS

| | | |
|---|---|---|
| JP | S48-70756 A | 9/1973 |
| JP | S63-68576 A | 3/1988 |
| JP | 2004-500471 A | 1/2004 |
| JP | 2014-025032 A | 2/2014 |
| JP | 2019-052235 A | 4/2019 |
| WO | WO-2019/054290 A1 | 3/2019 |

OTHER PUBLICATIONS

Genesty et al., "Preparation of a Stable Diaryl Trisulfide from a Sacrificial Sulfur Cathode and 2-Chloropyrimidine," Acta Chemica Scandinavica, vol. 53, 1999, pp. 952-954.

International Searching Authority, "International Search Report," issued in connection with International Patent Application No. PCT/JP2020/022037, dated Jul. 7, 2020.

International Searching Authority, "Written Opinion," issued in connection with International Patent Application No. PCT/JP2020/022037, dated Jul. 7, 2020.

* cited by examiner

*Primary Examiner* — Doris L Lee
(74) *Attorney, Agent, or Firm* — Foley & Lardner LLP

(57) ABSTRACT

The present invention provides a compound represented by the formula (I), which compound is useful for improving the abrasion resistance of a vulcanized rubber composition (the symbols in the following formula are as defined in the description).

11 Claims, No Drawings

TRISULFIDE COMPOUND

CROSS-REFERENCE TO RELATED APPLICATIONS

The present application claims priority under 37 U.S.C. § 371 to International Patent Application No. PCT/JP2020/022037, filed Jun. 4, 2020, which claims priority to and the benefit of Japanese Patent Application No. 2019-107337, filed on Jun. 7, 2019. The contents of these applications are hereby incorporated by reference in their entireties.

TECHNICAL FIELD

The present invention relates to a trisulfide compound, and a rubber composition obtained by kneading a rubber component and the compound.

BACKGROUND ART

In the fields in which vulcanized rubber compositions are employed (e.g., tire industry), the abrasion resistance of such vulcanized rubber compositions is one of the important performance characteristics, and various techniques have been suggested to improve the abrasion resistance. For example, Patent Literature 1 discloses a rubber composition that contains a special rubber component, silica, and a silane coupling agent having a mercapto group.

CITATION LIST

Patent Literature

Patent Literature 1: Japanese Patent Laid-Open No. 2014-25032

SUMMARY OF INVENTION

Technical Problem

In the fields in which vulcanized rubber compositions are employed, such vulcanized rubber compositions are continually required to have improved abrasion resistance. The present invention has been made in view of the situation, and an object thereof is to provide a novel compound useful for improving the abrasion resistance of vulcanized rubber compositions.

Solution to Problem

The present invention that can achieve the above-described object is as follows.

[1] A compound represented by the formula (1):

[Formula 1]

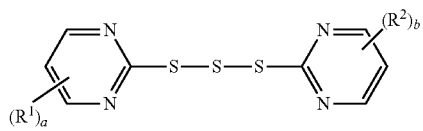

[wherein,
a and b each independently represent an integer of 1 to 3, and $R^1$ and $R^2$ each independently represent a halogen atom, a $C_{1-18}$ alkyl group optionally having a substituent, a $C_{3-10}$ cycloalkyl group optionally having a substituent, a $C_{6-18}$ aryl group optionally having a substituent, a $C_{7-20}$ aralkyl group optionally having a substituent, a carboxy group, a $C_{1-18}$ alkoxy-carbonyl group optionally having a substituent, a $C_{3-10}$ cycloalkyloxy-carbonyl group optionally having a substituent, a $C_{6-18}$ aryloxy-carbonyl group optionally having a substituent, a $C_{7-20}$ aralkyloxy-carbonyl group optionally having a substituent, a carbamoyl group optionally having a substituent, a hydroxy group, a $C_{1-18}$ alkoxy group optionally having a substituent, a $C_{3-10}$ cycloalkyloxy group optionally having a substituent, a $C_{6-18}$ aryloxy group optionally having a substituent, a $C_{7-20}$ aralkyloxy group optionally having a substituent, a $C_{1-18}$ alkyl-carbonyloxy group optionally having a substituent, a $C_{3-10}$ cycloalkyl-carbonyloxy group optionally having a substituent, a $C_{6-18}$ aryl-carbonyloxy group optionally having a substituent, a $C_{7-20}$ aralkyl-carbonyloxy group optionally having a substituent, an amino group optionally having a substituent, or a nitro group, when a is 2 or 3, a plurality of $R^1$'s each may be the same or different, and when b is 2 or 3, a plurality of $R^2$'s each may be the same or different.].

[2] The compound according to [1], wherein $R^1$ and $R^2$ are each independently a $C_{1-18}$ alkyl group optionally having a substituent, a hydroxy group, a $C_{1-18}$ alkoxy group optionally having a substituent, a $C_{1-18}$ alkyl-carbonyloxy group optionally having a substituent, an amino group, or a mono ($C_{1-18}$ alkyl-carbonyl)amino group (the $C_{1-18}$ alkyl optionally has a substituent), more preferably a $C_{1-18}$ alkyl group, a hydroxy group, a $C_{1-18}$ alkoxy group, a $C_{1-18}$ alkyl-carbonyloxy group, an amino group, or a mono($C_{1-18}$ alkyl-carbonyl)amino group, when a is 2 or 3, a plurality of $R^1$'s each may be the same or different, and when b is 2 or 3, a plurality of $R^2$'s each may be the same or different.

[3] The compound according to [1], wherein $R^1$ and $R^2$ are each independently a $C_{1-6}$ alkyl group, when a is 2 or 3, a plurality of $R^1$'s each may be the same or different, and when b is 2 or 3, a plurality of $R^2$'s each may be the same or different.

[4] The compound according to any one of [1] to [3], wherein both a and b are 2.

[5] The compound according to any one of [1] to [3], wherein the formula (Ia):

[Formula 2]

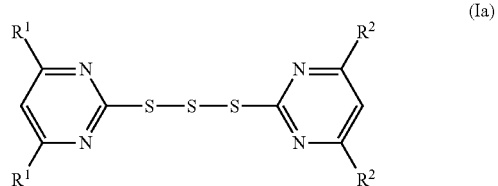

[wherein, $R^1$ and $R^2$ are as defined above.].

[6] The compound according to any one of [1] to [5], wherein the plurality of $R^1$'s are the same.

[7] The compound according to any one of [1] to [6], wherein the plurality of $R^2$'s are the same.

[8] The compound according to any one of [1] to [7], wherein $R^1$ and $R^2$ are the same.

[9] A rubber composition obtained by kneading a rubber component, a vulcanization accelerator, silica, and a compound represented by the formula (II):

[Formula 3]

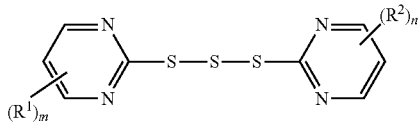

(II)

[wherein,
m and n each independently represent an integer of 1 to 3, and
$R^1$ and $R^2$ each independently represent a halogen atom, a $C_{1-18}$ alkyl group optionally having a substituent, a $C_{3-10}$ cycloalkyl group optionally having a substituent, a $C_{6-18}$ aryl group optionally having a substituent, a $C_{7-20}$ aralkyl group optionally having a substituent, a carboxy group, a $C_{1-18}$ alkoxy-carbonyl group optionally having a substituent, a $C_{3-10}$ cycloalkyloxy-carbonyl group optionally having a substituent, a $C_{6-18}$ aryloxy-carbonyl group optionally having a substituent, a $C_{7-20}$ aralkyloxy-carbonyl group optionally having a substituent, a carbamoyl group optionally having a substituent, a hydroxy group, a $C_{1-18}$ alkoxy group optionally having a substituent, a $C_{3-10}$ cycloalkyloxy group optionally having a substituent, a $C_{6-18}$ aryloxy group optionally having a substituent, a $C_{7-20}$ aralkyloxy group optionally having a substituent, a $C_{1-18}$ alkyl-carbonyloxy group optionally having a substituent, a $C_{3-10}$ cycloalkyl-carbonyloxy group optionally having a substituent, a $C_{6-18}$ aryl-carbonyloxy group optionally having a substituent, a $C_{7-20}$ aralkyl-carbonyloxy group optionally having a substituent, an amino group optionally having a substituent, or a nitro group, when m is 2 or 3, a plurality of $R^1$'s each may be the same or different, and when n is 2 or 3, a plurality of $R^2$'s each may be the same or different.].

[10] The rubber composition according to [9], wherein $R^1$ and $R^2$ are each independently a $C_{1-18}$ alkyl group optionally having a substituent, a hydroxy group, a $C_{1-18}$ alkoxy group optionally having a substituent, a $C_{1-18}$ alkyl-carbonyloxy group optionally having a substituent, an amino group, or a mono($C_{1-18}$ alkyl-carbonyl)amino group (the $C_{1-18}$ alkyl optionally has a substituent), more preferably a $C_{1-18}$ alkyl group, a hydroxy group, a $C_{1-18}$ alkoxy group, a $C_{1-18}$ alkyl-carbonyloxy group, an amino group, or a mono($C_{1-18}$ alkyl-carbonyl)amino group, when m is 2 or 3, a plurality of $R^1$'s each may be the same or different, and when n is 2 or 3, a plurality of $R^2$'s each may be the same or different.

[11] The rubber composition according to [9], wherein $R^1$ and $R^2$ are each independently a $C_{1-6}$ alkyl group, when m is 2 or 3, a plurality of $R^1$'s each may be the same or different, and when n is 2 or 3, a plurality of $R^2$'s each may be the same or different.

[12] The rubber composition according to any one of [9] to [11], wherein m and n are each independently an integer of 1 to 3.

[13] The rubber composition according to any one of [9] to [11], wherein both m and n are 2.

[14] The rubber composition according to any one of [9] to [11], wherein the compound represented by the formula (II) is a compound represented by the formula (Ia):

[Formula 4]

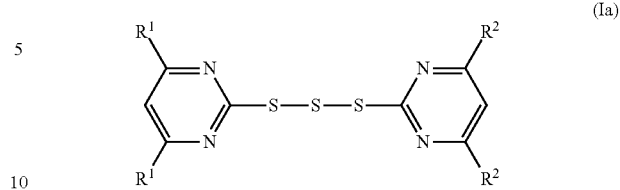

(Ia)

[wherein, $R^1$ and $R^2$ are as defined above.].

[15] The rubber composition according to any one of [9] to [14], wherein the plurality of $R^1$'s are the same.

[16] The rubber composition according to any one of [9] to [15], wherein the plurality of $R^2$'s are the same.

[17] The rubber composition according to any one of [9] to [16], wherein $R^1$ and $R^2$ are the same.

[18] The rubber composition according to any one of [9] to [17], wherein the amount of the compound represented by the formula (II) is 0.02 to 10 parts by weight, more preferably 0.02 to 8 parts by weight, further preferably 0.1 to 6 parts by weight, and particularly preferably 0.1 to 5 parts by weight per 100 parts by weight of the rubber component.

[19] The rubber composition according to any one of [9] to [18], wherein the rubber component contains a diene-based rubber.

[20] The rubber composition according to [19], wherein the amount of the diene-based rubber in the rubber component is 50 to 100% by weight, more preferably 70 to 100% by weight, further preferably 80 to 100% by weight, and most preferably 100% by weight.

[21] The rubber composition according to any one of [9] to [18], wherein the rubber component contains a styrene-butadiene copolymer rubber.

[22] The rubber composition according to [21], wherein the amount of the styrene-butadiene copolymer rubber in the rubber component is 50 to 100% by weight, more preferably 70 to 100% by weight, further preferably 80 to 100% by weight, and most preferably 100% by weight.

[23] The rubber composition according to any one of [9] to [18], wherein the rubber component contains a styrene-butadiene copolymer rubber and a butadiene rubber.

[24] The rubber composition according to [23], wherein the total amount of the styrene-butadiene copolymer rubber and butadiene rubber in the rubber component is 50 to 100% by weight, more preferably 70 to 100% by weight, further preferably 80 to 100% by weight, and most preferably 100% by weight.

[25] The rubber composition according to [23] or [24], wherein the weight ratio of the amount of butadiene rubber to the amount of the styrene-butadiene copolymer rubber (the amount of the butadiene rubber/the amount of the styrene-butadiene copolymer rubber) is 5/95 to 50/50, more preferably 10/90 to 40/60, and further preferably 20/80 to 40/60.

[26] The rubber composition according to any one of [9] to [25], wherein the amount of the vulcanization accelerator is 0.5 to 10.5 parts by weight, more preferably 0.7 to 8 parts by weight, further preferably 0.8 to 6 parts by weight, and particularly preferably 0.8 to 5.5 parts by weight per 100 parts by weight of the rubber component.

[27] The rubber composition according to any one of [9] to [26], wherein the vulcanization accelerator contains a sulfenamide-based vulcanization accelerator.

[28] The rubber composition according to [27], wherein the sulfenamide-based vulcanization accelerator is at least one selected from the group consisting of N-cyclohexyl-2-benzothiazolylsulfenamide (CBS), N-tert-butyl-2-benzothiazolylsulfenamide (BBS), N-oxydiethylene-2-benzothiazolylsulfenamide (OBS), and N,N-dicyclohexyl-2-benzothiazolylsulfenamide (DCBS), and more preferably N-cyclohexyl-2-benzothiazolylsulfenamide (CBS).

[29] The rubber composition according to [27] or [28], wherein the amount of the sulfenamide-based vulcanization accelerator is 0.1 to 10 parts by weight, more preferably 0.1 to 7 parts by weight, further preferably 0.1 to 5 parts by weight, and particularly preferably 0.5 to 5 parts by weight per 100 parts by weight of the rubber component.

[30] The rubber composition according to any one of [9] to [29], wherein the silica has a BET specific surface area of 20 to 400 m$^2$/g, more preferably 20 to 350 m$^2$/g, and further preferably 20 to 300 m$^2$/g.

[31] The rubber composition according to any one of [9] to [30], wherein the amount of the silica is 10 to 120 parts by weight, more preferably 20 to 120 parts by weight, further preferably 30 to 120 parts by weight, particularly preferably 40 to 100 parts by weight, and most preferably 50 to 100 parts by weight per 100 parts by weight of the rubber component.

[32] The rubber composition according to any one of [9] to [31] obtained by kneading additionally carbon black.

[33] The rubber composition according to [32], wherein the carbon black has a BET specific surface area of 10 to 130 m$^2$/g, more preferably 20 to 130 m$^2$/g, and further preferably 40 to 130 m$^2$/g.

[34] The rubber composition according to [32] or [33], wherein the amount of the carbon black is 1 to 40 parts by weight, more preferably 1 to 30 parts by weight, and further preferably 1 to 25 parts by weight per 100 parts by weight of the rubber component.

[35] The rubber composition according to any one of [32] to [34], wherein the weight ratio of the amount of the carbon black to the amount of the silica (the amount of the carbon black/the amount of the silica) is 1/120 to 3/4, more preferably 1/100 to 1/2, further preferably 1/100 to 5/12.

[36] The rubber composition according to any one of [9] to [35] obtained by kneading additionally a sulfur component.

[37] The rubber composition according to [36], wherein the amount of the sulfur component is 0.1 to 5 parts by weight, more preferably 0.1 to 3 parts by weight, and further preferably 0.1 to 2 parts by weight per 100 parts by weight of the rubber component.

[38] The rubber composition according to [36] or [37], wherein the weight ratio of the amount of the sulfur component to the amount of the vulcanization accelerator (the amount of the sulfur component/the amount of the vulcanization accelerator) is 1/10 to 10/1 and more preferably 1/5 to 5/1.

[39] A vulcanized rubber composition obtained by vulcanizing the rubber composition according to any one of [36] to [38].

[40] A tire comprising the vulcanized rubber composition according to [39].

Advantageous Effect of Invention

Use of the compound of the present invention can provide improved abrasion resistance of the vulcanized rubber composition.

DESCRIPTION OF EMBODIMENT

The present invention provides the following:
(1) a compound represented by the above formula (I),
(2) a rubber composition obtained by kneading a rubber component, a vulcanization accelerator, silica, a compound represented by the above formula (II), and as required, other components,
(3) a rubber composition obtained by kneading a rubber component, a vulcanization accelerator, silica, a compound represented by the above formula (II), a sulfur component, and as required, other components,
(4) a vulcanized rubber composition obtained by vulcanizing the rubber composition according to (3), and
(5) a tire comprising the vulcanized rubber composition according to (4).

Hereinafter, a "compound represented by the formula (I)", may be abbreviated as the "compound (I)". Compounds and the like represented by other formulas may be abbreviated in the same manner.

The aforementioned compound (I) and compound (II) are the same except that a and b in the formula (I) are each independently an integer of 1 to 3 and m and n in the formula (II) are each independently an integer of 0 to 3. Here, "m is 0" means that $R^1$ is not present, and "n is 0" means that $R^2$ is not present.

Hereinafter, the present invention will be described in sequence. The following exemplification, preferable descriptions, and the like described below may be combined, unless these do not conflict with each other.

Definitions

First, definitions of groups and the like used the present description will be described.

"$C_{x-y}$" means that the number of carbon atoms is x or more and y or less (x and y each represent a number).

Examples of a halogen atom include a fluorine atom, a chlorine atom, a bromine atom, and an iodine atom.

An alkyl group may be either of linear and branched. The number of carbon atoms of the alkyl group is 1 to 18, for example. Examples of the alkyl group include a methyl group, an ethyl group, a propyl group, an isopropyl group, a butyl group, an isobutyl group, a sec-butyl group, a tert-butyl group, a pentyl group, an isopentyl group, a neopentyl group, a 1-ethylpropyl group, a hexyl group, an isohexyl group, a 1,1-dimethylbutyl group, a 2,2-dimethylbutyl group, a 3,3-dimethylbutyl group, a 2-ethylbutyl group, a heptyl group, an octyl group, a nonyl group, a decyl group, an undecyl group, a dodecyl group, a tridecyl group, a tetradecyl group, a pentadecyl group, a hexadecyl group, a heptadecyl group, and an octadecyl group.

The alkyl group optionally has a substituent. Other groups containing an alkyl group as a moiety (e.g. an alkoxy group) also optionally have a substituent. Examples of substituents that may be possessed by the alkyl groups (e.g., $C_{1-18}$ alkyl groups) and other groups containing an alkyl group (e.g., $C_{1-18}$ alkyl group) as a moiety include the following:
(1) a halogen atom,
(2) a cycloalkyl group (preferably a $C_{3-8}$ cycloalkyl group),
(3) an alkoxy group (preferably a $C_{1-6}$ alkoxy group), (4) a cycloalkyloxy group (preferably a $C_{3-8}$ cycloalkyloxy group),
(5) an aryloxy group (preferably a $C_{6-14}$ aryloxy group),
(6) an aralkyloxy group (preferably a $C_{7-16}$ aralkyloxy group), and (7) an amino group optionally having a substituent.

The number of carbon atoms of the cycloalkyl group is 3 to 10, for example. Examples of the cycloalkyl group include a cyclopropyl group, a cyclobutyl group, a cyclopentyl group, a cyclohexyl group, a cycloheptyl group, a cyclooctyl group, a bicyclo[2.2.1]heptyl group, a bicyclo[2.2.2]octyl group, a bicyclo[3.2.1]octyl group, and an adamantyl group.

The number of carbon atoms of the aryl group is 6 to 18, for example. Examples of the aryl group include a phenyl group, a 1-naphthyl group, a 2-naphthyl group, a 1-anthryl group, a 2-anthryl group, and a 9-anthryl group.

The number of carbon atoms of the aralkyl group is 7 to 20, for example. Examples of the aralkyl group include a benzyl group, a phenethyl group, a naphthylmethyl group, and a phenylpropyl group.

The cycloalkyl group, aryl group, and aralkyl group each optionally have a substituent. Other groups containing a cycloalkyl group or the like as a moiety (e.g., cycloalkyloxy group or the like) also optionally have a substituent. Examples of substituents that may be possessed by the cycloalkyl group (e.g., $C_{3-10}$ cycloalkyl group), aryl group (e.g., $C_{6-18}$ aryl group), and aralkyl group (e.g., $C_{7-20}$ aralkyl group) and other groups containing such a group as a moiety include the following:
(1) a halogen atom,
(2) an alkyl group (preferably a $C_{1-6}$ alkyl group),
(3) a cycloalkyl group (preferably a $C_{3-8}$ cycloalkyl group),
(4) an aryl group (preferably a $C_{6-14}$ aryl group),
(5) an aralkyl group (preferably a $C_{7-16}$ aralkyl group),
(6) an alkoxy group (preferably a $C_{1-6}$ alkoxy group),
(7) a cycloalkyloxy group (preferably a $C_{3-8}$ cycloalkyloxy group),
(8) an aryloxy group (preferably a $C_{6-14}$ aryloxy group),
(9) an aralkyloxy group (preferably a $C_{7-16}$ aralkyloxy group), and
(10) an amino group optionally having a substituent.

The description of an alkyl group as a moiety of an alkoxy group (i.e., alkyloxy group) is as described above. The same applies to the description of an alkyl group as a moiety of a group described below. Examples of the alkoxy group include a methoxy group, an ethoxy group, a propoxy group, an isopropoxy group, a butoxy group, an isobutoxy group, a sec-butoxy group, a tert-butoxy group, a pentyloxy group, and a hexyloxy group.

The description of a cycloalkyl group as a moiety of a cycloalkyloxy group is as described above. The same applies to the description of a cycloalkyl group as a moiety of a group described below. Examples of the cycloalkyloxy group include a cyclopropyloxy group, a cyclobutyloxy group, a cyclopentyloxy group, a cyclohexyloxy group, a cycloheptyloxy group, and a cyclooctyloxy group.

The description of an aryl group as a moiety of an aryloxy group is as described above. The same applies to the description of an aryl group as a moiety of a group described below. Examples of the aryloxy group include a phenyloxy group, a 1-naphthyloxy group, and a 2-naphthyloxy group.

The description of an aralkyl group as a moiety of an aralkyloxy group is as described above. The same applies to the description of an aralkyl group as a moiety of a group described below. Examples of the aralkyloxy group include a benzyloxy group, a phenethyloxy group, a naphthylmethyloxy group, and a phenylpropyloxy group.

Examples of the alkyl-carbonyloxy group include an acetyloxy group, a propanoyloxy group, a butanoyloxy group, a 2-methylpropanoyloxy group, a pentanoyloxy group, a 3-methylbutanoyloxy group, a 2-methylbutanoyloxy group, a 2,2-dimethylpropanoyloxy group, a hexanoyloxy group, and a heptanoyloxy group. A reference to a "$C_{1-18}$ alkyl-carbonyloxy group" means that the number of carbon atoms of the alkyl group as a moiety of this group is 1 to 18. Other references have the same meaning.

Examples of the cycloalkyl-carbonyloxy group include a cyclopropyl-carbonyloxy group, a cyclobutyl-carbonyloxy group, a cyclopentyl-carbonyloxy group, a cyclohexyl-carbonyloxy group, a cycloheptyl-carbonyloxy group, and a cyclooctyl-carbonyloxy group.

Examples of the aryl-carbonyloxy group include a benzoyloxy group, a 1-naphthoyloxy group, and a 2-naphthoyloxy group.

Examples of the aralkyl-carbonyloxy group include a phenylacetyloxy group and a phenylpropionyloxy group.

Examples of the alkoxy-carbonyl group include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, and a hexyloxycarbonyl group.

Examples of the cycloalkyloxy-carbonyl group include a cyclopropyloxycarbonyl group, a cyclobutyloxycarbonyl group, a cyclopentyloxycarbonyl group, a cyclohexyloxycarbonyl group, a cycloheptyloxycarbonyl group, and a cyclooctyloxycarbonyl group.

Examples of the aryloxy-carbonyl group include a phenyloxycarbonyl group, a 1-naphthyloxycarbonyl group, and a 2-naphthyloxycarbonyl group.

Examples of the aralkyloxy-carbonyl group include a benzyloxycarbonyl group, a phenethyloxycarbonyl group, a naphthylmethyloxycarbonyl group, and a phenylpropyloxycarbonyl group.

Examples of the carbamoyl group optionally having a substituent include carbamoyl groups optionally having one or two substituents selected from an alkyl group optionally having a substituent, a cycloalkyl group optionally having a substituent, an aryl group optionally having a substituent, and an aralkyl group optionally having a substituent.

Preferred examples of the carbamoyl group optionally having a substituent include the following:
(1) a carbamoyl group,
(2) a mono- or di-(alkyl)carbamoyl group (the alkyl optionally has a substituent) (e.g., a methylcarbamoyl group, an ethylcarbamoyl group, a dimethylcarbamoyl group, a diethylcarbamoyl group, and a N-ethyl-N-methylcarbamoyl group),
(3) a mono- or di-(cycloalkyl)carbamoyl group (the cycloalkyl optionally has a substituent) (e.g., a cyclopropylcarbamoyl group and a cyclohexylcarbamoyl group),
(4) a mono- or di-(aryl)carbamoyl group (the aryl optionally has a substituent) (e.g., a phenylcarbamoyl group), and
(5) a mono- or di-(aralkyl)carbamoyl group (the aralkyl optionally has a substituent) (e.g., a benzylcarbamoyl group and a phenethylcarbamoyl group).

Here, the "mono- or di-(alkyl)carbamoyl group (the alkyl optionally has a substituent)" represents a mono(alkyl)carbamoyl group (the alkyl optionally has a substituent) or a di(alkyl)carbamoyl group (the alkyl optionally has a substituent). The "mono(alkyl)carbamoyl group (the alkyl optionally has a substituent)" represents a carbamoyl group having an alkyl group optionally having a substituent, and the "di(alkyl)carbamoyl group (the alkyl optionally has a substituent)" represents a carbamoyl group having two alkyl groups optionally having a substituent. Other like references have the same meaning.

Examples of the amino group optionally having a substituent include one or two amino groups optionally having a substituent selected from an alkyl group optionally having a substituent, a cycloalkyl group optionally having a substituent, an aryl group optionally having a substituent, an aralkyl group optionally having a substituent, an alkyl-carbonyl group optionally having a substituent, a cycloalkyl-carbonyl group optionally having a substituent, an aryl-carbonyl group optionally having a substituent, and an aralkyl-carbonyl group optionally having a substituent.

Preferred examples of the amino group optionally having a substituent include the following:

(1) an amino group,
(2) a mono- or di-(alkyl)amino group (the alkyl optionally has a substituent) (e.g., a methylamino group, a trifluoromethylamino group, a dimethylamino group, an ethylamino group, a diethylamino group, a propylamino group, and a dibutylamino group),
(3) a mono- or di-(cycloalkyl)amino group (the cycloalkyl optionally has a substituent) (e.g., a cyclopropylamino group and a cyclohexylamino group),
(4) a mono- or di-(aryl)amino group (the aryl optionally has a substituent) (e.g., a phenylamino group),
(5) a mono- or di-(aralkyl)amino group (the aralkyl optionally has a substituent) (e.g., a benzylamino group and a dibenzylamino group),
(6) a mono- or di-(alkyl-carbonyl)amino group (the alkyl optionally has a substituent) (e.g., an acetylamino group and a propionyl amino group),
(7) a mono- or di-(cycloalkyl-carbonyl)amino group (the cycloalkyl optionally has a substituent) (e.g., a cyclopropylcarbonylamino group and a cyclohexylcarbonylamino group),
(8) a mono- or di-(aryl-carbonyl)amino group (the aryl optionally has a substituent) (e.g., a benzoylamino group), and
(9) a mono- or di-(aralkyl-carbonyl)amino group (the aralkyl optionally has a substituent) (e.g., benzylcarbonylamino group).

Here, the "mono- or di-(alkyl)amino group (the alkyl optionally has a substituent)" represents a mono(alkyl)amino group (the alkyl optionally has a substituent) or a di(alkyl)amino group (the alkyl optionally has a substituent). The "mono(alkyl)amino group (the alkyl optionally has a substituent)" represents an amino group having an alkyl group optionally having a substituent, and the "di(alkyl)amino group (the alkyl optionally has a substituent)" represents an amino group having two alkyl groups optionally having a substituent. Other like references have the same meaning.

<Compound (I) and Compound (II)>

The compound of the present invention is a compound represented by the formula (I):

[Formula 5]

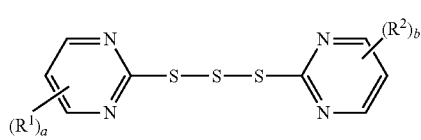

(I)

One compound (I) may be used singly, or two or more compounds (I) may be used.

a and b in the formula (I) each independently represent 1 to 3. When a is 2 or more, a plurality of $R^1$'s each may be the same or different, and when b is 2 or more, a plurality of $R^2$'s each may be the same or different. The plurality of $R^1$'s are preferably the same. The plurality of $R^2$'s are preferably the same. Both a and b are preferably 2.

$R^1$ and $R^2$ in the formula (1) each independently represent a halogen atom, a $C_{1-18}$ alkyl group optionally having a substituent, a $C_{3-10}$ cycloalkyl group optionally having a substituent, a $C_{6-18}$ aryl group optionally having a substituent, a $C_{7-20}$ aralkyl group optionally having a substituent, a carboxy group, a $C_{1-18}$ alkoxy-carbonyl group optionally having a substituent, a $C_{3-10}$ cycloalkyloxy-carbonyl group optionally having a substituent, a $C_{6-18}$ aryloxy-carbonyl group optionally having a substituent, a $C_{7-20}$ aralkyloxy-carbonyl group optionally having a substituent, a carbamoyl group optionally having a substituent, a hydroxy group, a $C_{1-18}$ alkoxy group optionally having a substituent, a $C_{3-10}$ cycloalkyloxy group optionally having a substituent, a $C_{6-18}$ aryloxy group optionally having a substituent, a $C_{7-20}$ aralkyloxy group optionally having a substituent, a $C_{1-18}$ alkyl-carbonyloxy group optionally having a substituent, a $C_{3-10}$ cycloalkyl-carbonyloxy group optionally having a substituent, a $C_{6-18}$ aryl-carbonyloxy group optionally having a substituent, a $C_{7-20}$ aralkyl-carbonyloxy group optionally having a substituent, an amino group optionally having a substituent, or a nitro group. $R^1$ and $R^2$ are preferably the same.

$R^1$ and $R^2$ are each independently preferably a $C_{1-18}$ alkyl group optionally having a substituent, a hydroxy group, a $C_{1-18}$ alkoxy group optionally having a substituent, a $C_{1-18}$ alkyl-carbonyloxy group optionally having a substituent, an amino group, or a mono($C_{1-18}$ alkyl-carbonyl)amino group (the $C_{1-18}$ alkyl optionally has a substituent), more preferably a $C_{1-18}$ alkyl group, a hydroxy group, a $C_{1-18}$ alkoxy group, a $C_{1-18}$ alkyl-carbonyloxy group, an amino group, or a mono($C_{1-18}$ alkyl-carbonyl)amino group, and further preferably a $C_{1-6}$ alkyl group. $R^1$ and $R^2$ are preferably the same.

Among compounds (I), from the viewpoint of the abrasion resistance of the vulcanized rubber composition, a compound represented by the following formula (Ia) is preferred ($R^1$ and $R^2$ in the following formula (Ia) are as defined above).

[Formula 6]

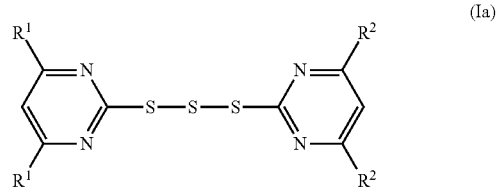

(Ia)

A trisulfide compound that may be used for production of the rubber composition of the present invention is a compound represented by the formula (II):

[Formula 7]

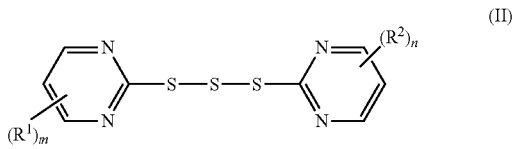

One compound (II) may be used singly, or two or more compounds (II) may be used.

As mentioned above, the compound (I) and compound (II) are the same except that a and b in the formula (I) are each independently an integer of 1 to 3 and m and n in the formula (II) are each independently an integer of 0 to 3. Thus, the description of $R^1$ and $R^2$ in the formula (II) are the same as the description of the $R^1$ and $R^2$ in the formula (I) mentioned above.

It is preferable that m and n in the formula (II) be each independently an integer of 1 to 3 (i.e., compound (II) =compound (I)). Both m and n are preferably 2, and the compound (II) is more preferably the compound (Ia).

The amount of the compound (II) (when two or more compounds (II) is used, the total amount thereof) is preferably 0.02 to 10 parts by weight, more preferably 0.02 to 8 parts by weight, further preferably 0.1 to 6 parts by weight, and particularly preferably 0.1 to 5 parts by weight per 100 parts by weight of the rubber component, from the viewpoint of the abrasion resistance of the vulcanized rubber composition.

The compound (I) and compound (II) each can be synthesized by converting a corresponding disulfide compound into a trisulfide compound. Hereinafter, a method for producing the compound (II) using a disulfide compound as a starting material will be described.

The compound (II) can be produced by, for example, reacting triphenylmethanesulfenyl chloride with a disulfide compound (ii) as shown below (the definition of the groups in the following formula is as described above).

[Formula 8]

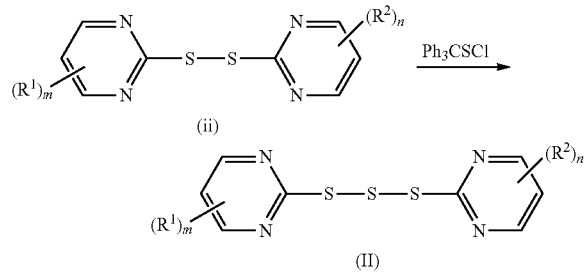

The amount of triphenylmethanesulfenyl chloride to be used is preferably 0.5 to 5.0 mol and more preferably 1.0 to 3.0 mol with respect to 1 mol of the disulfide compound (ii).

The above reaction (i.e., conversion from a disulfide compound to a trisulfide compound) is usually conducted in a solvent. Examples of the solvent include halogenated hydrocarbon-based solvents such as chloroform, dichloromethane, 1,2-dichloroethane, 1,1,2,2-tetrachloroethane, chlorobenzene, 1,2-dichlorobenzene, 1,3-dichlorobenzene, and 1,4-dichlorobenzene, hydrocarbon-based solvents such as hexane, benzene, toluene, and xylene, and ether-based solvents such as tetrahydrofuran, 1,4-dioxane, and ethyl methyl ether. One solvent may be used singly, or two or more solvents may be used. The above reaction is preferably conducted under an inert gas (e.g., nitrogen) atmosphere.

The temperature for the above reaction (i.e., conversion from a disulfide compound to a trisulfide compound) may depend on a solvent to be used. In use of a halogenated hydrocarbon-based solvent such as chloroform, the reaction is preferably allowed to proceed while refluxed with heating. The period for the reaction is preferably 1 to 24 hours and more preferably 1 to 8 hours.

After the reaction, the compound (II) can be obtained by a known means (e.g., extraction, concentration, or filtration). The resulting compound (II) may be purified by a known means (e.g., silica gel column chromatography).

As the disulfide compound (ii) as the starting material, a commercially available product may be used. Alternatively, the disulfide compound (ii) may be produced by a known reaction. The disulfide compound (ii) can be produced by, for example, a reaction as shown below (the definition of the groups in the following formula is as described above).

[Formula 9]

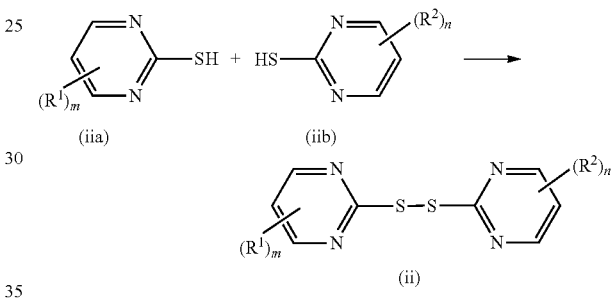

The above reaction is oxidization of the compound (iia) and compound (iib) and formation of a disulfide bond. This oxidization may be conducted by using an oxidizing agent such as hydrogen peroxide, potassium ferricyanide, oxygen, iodine, bromine, iodobenzene diacetate, sodium periodate, or potassium permanganate. One oxidizing agent may be used singly, or two or more oxidizing agents may be used. Alternatively, hydrogen peroxide and sodium iodide may be combined to generate iodine in the system. The amount of the oxidizing agent to be used (when two or more oxidizing agents are used, the total amount thereof) is preferably 1 to 10 mol and more preferably 1 to 3 mol with respect to 1 mol in total of the compound (iia) and the compound (iib).

The above reaction (i.e., oxidization and formation of a disulfide bond) is conducted usually in a solvent. Examples of this solvent include ester-based solvents such as ethyl acetate, methyl acetate, butyl acetate, propyl acetate, isopropyl acetate, and ethyl lactate, amide-based solvents such as N,N-dimethylformamide, N,N-dimethylacetamide, and N-methyl-2-pyrrolidone, sulfoxide-based solvents such as dimethylsulfoxide, aromatic hydrocarbon solvents such as benzene, toluene, and xylene, ether-based solvents such as tetrahydrofuran, 1,4-dioxane, and methyl ethyl ether, and protic solvents such as water, methanol, and ethanol. One solvent may be used singly, or two or more solvents may be used.

The reaction (i.e., oxidization and formation of a disulfide bond) is preferably conducted by adding a hydrogen peroxide aqueous solution to the compound (iia) and the compound (iib). The oxidization and formation of a disulfide bond by use of a hydrogen peroxide aqueous solution is an exothermic reaction. After addition of the hydrogen peroxide aqueous solution, the mixture is preferably stirred at 0 to 100° C. and more preferably 0 to 60° C. for preferably 0.1 to 48 hours and more preferably 0.1 to 24 hours.

After the reaction, the disulfide compound (ii) can be obtained by a known means (e.g., extraction, concentration, or filtration). The resulting disulfide compound (ii) may be purified by a known means.

<Rubber Component>

Examples of the rubber component include a styrene-butadiene copolymer rubber (SBR), a natural rubber (NR) (modified natural rubber including, for example, epoxidized natural rubber and deproteinized natural rubber), a butadiene rubber (BR), an isoprene rubber (IR), a nitrile rubber (NBR), a chloroprene rubber (CR), an isoprene-isobutyrene copolymer rubber (IIR), an ethylene-propylene-diene copolymer rubber (EPDM), and a halogenated butyl rubber (HR). One alone rubber component or two or more rubber components may be used either singly or as combined.

Examples of the SBR include emulsion-polymerized SBRs and solution-polymerized SBRs described on pages 210 to 211 in Gomu Kogyo Binran (Rubber Industry Handbook), 4th edition edited by Society of Rubber Industry, Japan. An emulsion-polymer SBR and a solution-polymerized SBR may be used in combination.

Examples of the solution-polymerized SBR include modified solution-polymerized SBRs having at least one element of nitrogen, tin, and silicone at a molecular end, obtained by modification with a modifier. Examples of the modifier include lactam compounds, amide compounds, urea compounds, N,N-dialkylacrylamide compounds, isocyanate compounds, imide compounds, silane compounds having an alkoxy group, aminosilane compounds, combined modifiers of a tin compound and a silane compound having an alkoxy group, and combined modifiers of an alkylacrylamide compound and a silane compound having an alkoxy group. These modifiers may be used alone, or a plurality of these may be used. Specific examples of the modified solution-polymerized SBR include solution-polymerized SBRs obtained by modifying a molecular end using 4,4'-bis(dialkylamino)benzophenone such as "Nipol® NS116" manufactured by Zeon Corporation, solution-polymerized SBRs obtained by modifying a molecular end using a halogenated tin compound such as "SL574" manufactured by JSR Corporation, and silane-modified solution-polymerized SBRs such as "E10" and "E15" manufactured by Asahi Kasei Corporation.

Also can be used are oil-extended SBRs obtained by adding an oil such as a process oil or an aroma oil to emulsion-polymerized SBRs and solution-polymerized SBRs.

Examples of the natural rubber include natural rubbers of RSS #1, RSS #3, TSR20, SIR20 grades or the like. Examples of epoxidized natural rubbers include those having a degree of epoxidation of 10 to 60 mol % (e.g., ENR25 and ENR50 manufactured by Kumpulan Guthrie Bhd.). Examples of deproteinized natural rubbers include deproteinized natural rubbers having a content of total nitrogen of 0.3% by weight or less. Examples of other modified natural rubbers include modified natural rubbers having a polar group obtained by reacting 4-vinylpyridine, N,N,-dialkylaminoethyl acrylate (e.g., N,N,-diethylaminoethyl acrylate), 2-hydroxy acrylate, or the like with a natural rubber.

As the BR, BRs that are common in the tire industry can be used. The BR is often used as a blend of a SBR and/or a natural rubber.

As the BR, BRs having a high cis content are preferred because of being highly effective for improving the abrasion resistance, and high-cis BRs having a high-cis content of 95% by mass or more are preferred. Examples of the high-cis BR include BR1220 manufactured by Zeon Corporation and BR150B manufactured by Ube Industries, Ltd.

It is also possible to use a modified BR having at least one element of nitrogen, tin, and silicone at a molecular end, obtained by modification with a modifier. Examples of the modifier include 4,4'-bis(dialkylamino)benzophenone, halogenated tin compounds, lactam compounds, amide compounds, urea compounds, N,N-dialkylacrylamide compounds, isocyanate compounds, imide compounds, silane compounds having an alkoxy group (e.g., a trialkoxysilane compound), aminosilane compounds, tin compounds, and alkylacrylamide compounds. These modifiers may be used alone, or a plurality of these may be used. Examples of the modified BR include tin-modified BRs such as "Nipol® BR1250H" manufactured by Zeon Corporation The rubber component preferably contains a diene-based rubber. Here, the diene-based rubber means a rubber produced from a diene monomer having a conjugated double bond as a raw material. Examples of the diene-based rubber include a styrene-butadiene copolymer rubber (SBR), a natural rubber (NR), a butadiene rubber (BR), an isoprene rubber (IR), a nitrile rubber (NBR), and a chloroprene rubber.

When a diene-based rubber is used, the amount of the diene-based rubber in the rubber component (i.e., the amount of the diene-based rubber per 100% by weight of the rubber component) is preferably 50 to 100% by weight, more preferably 70 to 100% by weight, further preferably 80 to 100% by weight, and most preferably 100% by weight. That is, the rubber component is most preferably constituted by a diene-based rubber.

In one aspect of the present invention, the rubber component preferably contains an SBR. In the present aspect, the amount of the SBR in the rubber component is preferably 50 to 100% by weight, more preferably 70 to 100% by weight, further preferably 80 to 100% by weight, and most preferably 100% by weight. That is, in the present aspect, the rubber component is most preferably constituted by a SBR.

In one aspect of the present invention, the rubber component preferably contains a SBR and a BR. In the present aspect, the total amount of the SBR and BR in the rubber component is preferably 50 to 100% by weight, more preferably 70 to 100% by weight, further preferably 80 to 100% by weight, and most preferably 100% by weight. That is, in the present aspect, the rubber component is most preferably constituted by a SBR and a BR. In the present aspect, the weight ratio of the amount of the BR to the amount of the SBR (the amount of the BR/the amount of the SBR) is preferably 5/95 to 50/50, more preferably 10/90 to 40/60 and further preferably 20/80 to 40/60, from the viewpoint of the abrasion resistance of the vulcanized rubber composition.

<Vulcanization Accelerator>

As the vulcanization accelerator, for example, those described in Gomu Kogyo Binran (Rubber Industry Handbook), 4th edition (published by The Society of Rubber Science and Technology, Japan, on Jan. 20, 1994) may be used. One vulcanization accelerator may be used singly, or two or more vulcanization accelerators may be used. Examples of the vulcanization accelerator include sulfenamide-based vulcanization accelerators, thiazole-based vulcanization accelerators, and guanidine-based vulcanization accelerators.

Examples of the sulfenamide-based vulcanization accelerator include N-cyclohexyl-2-benzothiazolylsulfenamide (CBS), N-tert-butyl-2-benzothiazolylsulfenamide (BBS), N-oxydiethylene-2-benzothiazolylsulfenamide (OBS), and N,N-dicyclohexyl-2-benzothiazolylsulfenamide (DCBS). One sulfenamide-based vulcanization accelerator singly, or two or more sulfenamide-based vulcanization accelerators may be used.

Examples of the thiazole-based vulcanization accelerator include 2-mercaptobenzothiazole (MBT), dibenzothiazolyl disulfide (MBTS), 2-mercaptobenzothiazole cyclohexylamine salts (CMBT), and 2-mercaptobenzothiazole zinc salts (ZMBT). One thiazole-based vulcanization accelerator may be used singly, or two or more thiazole-based vulcanization accelerators may be used.

Examples of the guanidine-based vulcanization accelerator include diphenylguanidine (DPG) and N,N'-di-o-tolyl guanidine (DOTG). One guanidine-based vulcanization accelerator may be used singly, or two or more guanidine-based vulcanization accelerator may be used.

The amount of the vulcanization accelerator (when two or more vulcanization accelerators are used, the total amount thereof) is preferably 0.5 to 10.5 parts by weight, more preferably 0.7 to 8 parts by weight, further preferably 0.8 to 6 parts by weight, and particularly preferably 0.8 to 5.5 parts by weight per 100 parts by weight of the rubber component.

The vulcanization accelerator preferably contains a sulfenamide-based vulcanization accelerator. The sulfenamide-based vulcanization accelerator is preferably at least one selected from the group consisting of N-cyclohexyl-2-benzothiazolylsulfenamide (CBS), N-tert-butyl-2-benzothiazolylsulfenamide (BBS), N-oxydiethylene-2-benzothiazolylsulfenamide (OBS), and N,N-dicyclohexyl-2-benzothiazolylsulfenamide (DCBS), and more preferably N-cyclohexyl-2-benzothiazolylsulfenamide (CBS).

When a sulfenamide-based vulcanization accelerator is used, the amount thereof (when two or more sulfenamide-based vulcanization accelerators are used, the total amount thereof) is preferably 0.1 to 10 parts by weight, more preferably 0.1 to 7 parts by weight, further preferably 0.1 to 5 parts by weight, and particularly preferably 0.5 to 5 parts by weight per 100 parts by weight of the rubber component.

The weight ratio of the amount of the sulfur component to the amount of the vulcanization accelerator (the amount of the sulfur component/the amount of the vulcanization accelerator) is not particularly limited and is preferably 1/10 to 10/1 and more preferably 1/5 to 5/1. When two or more vulcanization accelerators (e.g., CBS and DPG) are used, the weight ratio is calculated by using the amount of the sulfur component and the total amount of the two or more vulcanization accelerators.

<Filler>

One of characteristics of the present invention is use of silica as a filler for the rubber composition.

Silica has a BET specific surface area of preferably 20 to 400 m$^2$/g, more preferably 20 to 350 m$^2$/g, and further preferably 20 to 300 m$^2$/g. The BET specific surface area can be measured by a multipoint nitrogen adsorption method (BET method).

Examples of the silica include (i) silica having a pH of 6 to 8, (ii) silica containing 0.2 to 1.5% by weight of sodium, (iii) perfectly spherical silica having a circularity of 1 to 1.3, (iv) silica surface-treated with a silicone oil (e.g., dimethylsilicone oil), an organosilicon compound containing an ethoxysilyl group, an alcohol (e.g., ethanol, polyethylene glycol), or the like, and (v) mixtures of two or more silicas each having a different surface area. One alone silica or two or more silicas may be used either singly or as combined.

Examples of commercially available silica products include "Nipsil® AQ" and "Nipsil® AQ-N" manufactured by Tosoh Silica Corporation, "Ultrasil® VN3", "Ultrasil® VN3-G", "Ultrasil® 360", "Ultrasil® 7000", and "Ultrasil® 9100GR" manufactured by Evonik Industries AG, and "Zeosil® 115GR", "Zeosil® 1115MP", "Zeosil® 1205MP", and "Zeosil® Z85MP" manufactured by Solvay S.A.

The amount of silica is preferably 10 to 120 parts by weight, more preferably 20 to 120 parts by weight, further preferably 30 to 120 parts by weight, particularly preferably 40 to 100 parts by weight, and most preferably 50 to 100 parts by weight per 100 parts by weight of the rubber component, from the viewpoint of the abrasion resistance of the vulcanized rubber composition.

In the present invention, carbon black may be used as a filler for the rubber composition.

The carbon black has a BET specific surface area of preferably 10 to 130 m$^2$/g, more preferably 20 to 130 m$^2$/g, and further preferably 40 to 130 m$^2$/g. The BET specific surface area can be measured by a multipoint nitrogen adsorption method (BET method).

Examples of the carbon black include carbon blacks described on page 494 in Gomu Kogyo Binran (Rubber Industry Handbook), 4th edition edited by Society of Rubber Industry, Japan. One alone carbon black or two or more carbon blacks may be used either singly or as combined. As the carbon black, HAF (High Abrasion Furnace), SAF (Super Abrasion Furnace), ISAF (Intermediate SAF), ISAF-HM (Intermediate SAF-High Modulus), FEF (Fast Extrusion Furnace), MAF (Medium Abrasion Furnace), GPF (General Purpose Furnace), and SRF (Semi-Reinforcing Furnace) are preferred.

When carbon black is used, the amount thereof is preferably 1 to 40 parts by weight, more preferably 1 to 30 parts by weight, and further preferably 1 to 25 parts by weight per 100 parts by weight of the rubber component, from the viewpoint of abrasion resistance and reinforcing performance.

When carbon black is used, the weight ratio of the amount of the carbon black to the amount of the silica (the amount of the carbon black/the amount of the silica) is preferably 1/120 to 3/4, more preferably 1/100 to 1/2, and further preferably 1/100 to 5/12 from the viewpoint of the abrasion resistance of the vulcanized rubber composition.

In the present invention, other filler different from silica and carbon black may be used. Examples of other fillers include aluminum hydroxide, pulverized bituminous coal, talc, clay (particularly, calcined clay), and titanium oxide.

Examples of aluminum hydroxide include aluminum hydroxides having a nitrogen adsorption specific surface area of 5 to 250 m$^2$/g and a DOP oiling quantity of 50 to 100 ml/100 g.

The average particle size of the pulverized bituminous coal is preferably 0.001 mm or more, preferably 0.1 mm or less, more preferably 0.05 mm or less, and further preferably 0.01 mm or less. The average particle size of the pulverized bituminous coal is an average particle size on a mass basis as calculated from a particle size distribution measured in accordance with JIS Z 8815-1994.

The specific gravity of the pulverized bituminous coal is preferably 1.6 or less, more preferably 1.5 or less, and further preferably 1.3 or less. When a pulverized bituminous coal having a specific gravity of more than 1.6 is used, the specific gravity of the entire rubber composition increases. Use of a rubber composition having a large specific gravity may lead to deterioration in the fuel consumption efficiency of a tire to be obtained. The specific gravity of the pulverized bituminous coal is preferably 0.5 or more and more preferably 1.0 or more. When a pulverized bituminous coal having a specific gravity of less than 0.5 is used, processability on kneading may be degraded.

<Sulfur Component>

Examples of the sulfur component include powder sulfur, precipitated sulfur, colloidal sulfur, insoluble sulfur, and highly dispersible sulfur.

The amount of the sulfur component is preferably 0.1 to 5 parts by weight, more preferably 0.1 to 3 parts by weight, and further preferably 0.1 to 2 parts by weight per 100 parts by weight of the rubber component.

<Other Components>

In the rubber composition of the present invention, other components different from the aforementioned compound (II), rubber component, vulcanization accelerator, filler, and sulfur component may be used. As the other components, components known in the field of rubber can be used, and examples thereof include a compound that can be bonded to silica (e.g., silane coupling agent), a vulcanization accelerating aid, a resin, a viscoelasticity improving agent, an anti-aging agent, a processing aid, an oil, a wax, a peptizing agent, a retarder, a compound having oxyethylene units, and a catalyst (cobalt naphthenate and the like). One of each of the other components or two or more of each of the other components may be used either singly or as combined.

Examples of the compound that can be bonded to silica include bis(3-triethoxysilylpropyl)tetrasulfide (e.g., "Si-69" manufactured by Evonik Industries AG), bis(3-triethoxysilylpropyl)disulfide (e.g., "Si-75" manufactured by Evonik Industries AG), bis(3-diethoxymethylsilylpropyl)tetrasulfide, bis(3-diethoxymethylsilylpropyl)disulfide, 3-octanoylthiopropyltriethoxysilane (alias: "octanethioic acid S-[3-(triethoxysilyl)propyl]ester", e.g., "NXT Silane" manufactured by General Electric Silicones), octanethioic acid S-[3-{(2-methyl-1,3-propanedialkoxy)ethoxysilyl}propyl]ester, octanethioic acid S-[3-{(2-methyl-1,3-propanedialkoxy)methylsilyl}propyl]ester, methyltrimethoxysilane, methyltriethoxysilane, methyltriacetoxysilane, methyltributoxysilane, ethyltrimethoxysilane, ethyltriethoxysilane, isobutyltrimethoxysilane, isobutyltriethoxysilane, n-octyltrimethoxysilane, n-octyltriethoxysilane, vinyltrimethoxysilane, vinyltriethoxysilane, vinyltris(methoxyethoxy)silane, phenyltrimethoxysilane, phenyltriethoxysilane, phenyltriacetoxysilane, 3-methacryloxypropyltrimethoxysilane, 3-methacryloxypropyltriethoxysilane, 3-aminopropyltrimethoxysilane, 3-aminopropyltriethoxysilane, N-(2-aminoethyl)-3-aminopropyltrimethoxysilane, N-(2-aminoethyl)-3-aminopropyltriethoxysilane, (3-glycidoxypropyl)trimethoxysilane, (3-glycidoxypropyl)triethoxysilane, 2-(3,4-epoxycyclohexyl)ethyltrimethoxysilane, 2-(3,4-epoxycyclohexyl)ethyltriethoxysilane, 3-isocyanatopropyltrimethoxysilane, and 3-isocyanatopropyltriethoxysilane. Among these, bis(3-triethoxysilylpropyl)tetrasulfide (e.g., "Si-69" manufactured by Evonik Industries AG), bis(3-triethoxysilylpropyl)disulfide (e.g., "Si-75" manufactured by Evonik Industries AG), and 3-octanoylthiopropyltriethoxysilane (e.g., "NXT Silane" manufactured by General Electric Silicones) are preferred.

When a compound that can be bonded to silica is used, the amount of the compound is preferably 2 to 10 parts by weight per 100 parts by weight of the silica.

In addition to the compound that can be bonded to silica, a monohydric alcohol such as ethanol, butanol, and octanol; a polyhydric alcohol such as ethylene glycol, diethylene glycol, triethylene glycol, polyethylene glycol, polypropylene glycol, pentaerythritol, and polyether polyol; a N-alkylamine; an amino acid; a liquid polybutadiene having a carboxy-modified or amine-modified molecular end, or the like may be used.

Examples of the vulcanization accelerating aid include zinc oxide, citraconimide compounds, alkylphenol-sulfur chloride condensates, organic thiosulfate compounds, and compounds represented by the formula (III):

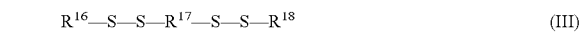

$$R^{16}\text{—S—S—}R^{17}\text{—S—S—}R^{18} \quad (III)$$

(wherein, $R^{17}$ represents a $C_{2-10}$ alkanediyl group, and $R^{16}$ and $R^{18}$ each independently represent a monovalent organic group containing a nitrogen atom).

In the present invention, zinc oxide is encompassed by the concept of the vulcanization accelerating aid and is not encompassed by the concept of the filler described above.

When zinc oxide is used, the amount of the zinc oxide is preferably 0.01 to 20 parts by weight, more preferably 0.1 to 15 parts by weight, and further preferably 0.1 to 10 parts by weight per 100 parts by weight of the rubber component.

As the citraconimide compound, biscitraconimides are preferred because of being thermally stable and excellent in dispersibility into a rubber component. Specific examples thereof include 1,2-biscitraconimide methylbenzene, 1,3-biscitraconimide methylbenzene, 1,4-biscitraconimide methylbenzene, 1,6-biscitraconimide methylbenzene, 2,3-biscitraconimide methyltoluene, 2,4-biscitraconimide methyltoluene, 2,5-biscitraconimide methyltoluene, 2,6-biscitraconimide methyltoluene, 1,2-biscitraconimide ethylbenzene, 1,3-biscitraconimide ethylbenzene, 1,4-biscitraconimide ethylbenzene, 1,6-biscitraconimide ethylbenzene, 2,3-biscitraconimide ethyltoluene, 2,4-biscitraconimide ethyltoluene, 2,5-biscitraconimide ethyltoluene, and 2,6-biscitraconimide ethyltoluene.

Among citraconimide compounds, 1,3-biscitraconimide methylbenzene represented by the following formula is preferred because of being particularly thermally stable, particularly excellent in dispersibility into a rubber component, and enabling a vulcanized rubber composition having a high hardness (Hs) to be obtained (Reversion suppression).

[Formula 10]

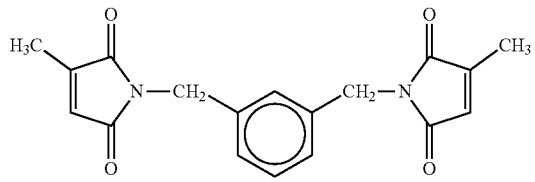

As the vulcanization accelerating aid, because of enabling a vulcanized rubber composition having a high hardness (Hs) to be obtained, an alkylphenol-sulfur chloride condensate represented by the formula (IV):

[Formula 11]

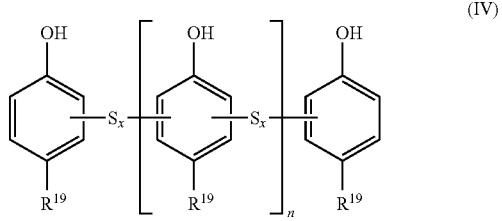

[wherein, n is an integer of 0 to 10, X is an integer of 2 to 4, and $R^{19}$ is a $C_{5-12}$ alkyl group.] is preferably used.

n in the formula (IV) is preferably an integer of 1 to 9 because the dispersibility of the alkylphenol-sulfur chloride condensate (IV) into a rubber component is good.

When X exceeds 4, the alkylphenol-sulfur chloride condensate (IV) tends to be thermally unstable. When X is 1, the sulfur content (the weight of sulfur) in the alkylphenol-sulfur chloride condensate (IV) is low. X is preferably 2 because a high hardness can be efficiently developed (reversion suppression).

$R^{19}$ is a $C_{5-12}$ alkyl group. $R^{19}$ is preferably a $C_{6-9}$ alkyl group because the dispersibility of the alkylphenol-sulfur chloride condensate (IV) into a rubber component is good.

A specific example of the alkylphenol-sulfur chloride condensate (IV) is TACKIROL V200 manufactured by Taoka Chemical Co., Ltd., in which, in the formula (IV), n is 0 to 10, X is 2, and $R^{19}$ is an octyl group and which has a sulfur content of 24% by weight.

As the vulcanization accelerating aid, a salt of organic thiosulfate compound (hereinafter, may be denoted by the "organic thiosulfate compound salt (V)") represented by the formula (V):

[wherein, s is an integer of 3 to 10.] is preferably used because a vulcanized rubber composition having a high hardness (Hs) can be obtained (reversion suppression). An organic thiosulfate compound salt (V) containing crystalline water may be used. Preferable examples of the organic thiosulfate compound salt (V) include lithium salts, potassium salts, sodium salts, magnesium salts, calcium salts, barium salts, zinc salts, nickel salts, and cobalt salt, and potassium salts and sodium salts are preferred.

s is an integer of 3 to 10 and preferably an integer of 3 to 6. When s is 2 or less, no sufficient thermal fatigue resistance tends to be obtained. When s is 11 or more, no sufficient effect of improving thermal fatigue resistance by the organic thiosulfate compound salt (V) may be obtained.

As the organic thiosulfate compound salt (V), from the viewpoint of being stable under normal temperature and pressure, a sodium salt monohydrate and a sodium salt dihydrate thereof are preferred. From the viewpoint of costs, an organic thiosulfate compound salt (V) obtained from sodium thiosulfate is more preferred, and sodium 1,6-hexamethylene dithiosulfate dihydrate represented by the following formula is further preferred.

[Formula 12]

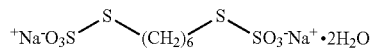

Because of being dispersed well into the rubber component and, when used in combination with an alkylphenol-sulfur chloride condensate (IV), being inserted at the midpoint of the —$S_X$-crosslinkage of the alkylphenol-sulfur chloride condensate (IV) to enable a hybrid crosslinkage with the alkylphenol-sulfur chloride condensate (IV) to be formed, a compound represented by the formula (III):

(wherein, $R^{17}$ represents a $C_{2-10}$ alkanediyl group, and $R^{16}$ and $R^{18}$ each independently represent a monovalent organic group containing a nitrogen atom.) is preferably used as the vulcanization accelerating aid.

$R^{17}$ is a $C_{2-10}$ alkanediyl group, preferably a $C_{4-8}$ alkanediyl group, and more preferably a linear $C_{4-8}$ alkanediyl group. $R^{17}$ is preferably linear. When $R^{17}$ has one or less carbon atom, thermal stability may be poor. When $R^{17}$ has 11 or more carbon atoms, the distance between polymers via the vulcanization accelerating aid becomes longer, and the effect of addition of the vulcanization accelerating aid may not be obtained.

$R^{16}$ and $R^{18}$ are each independently a monovalent organic group containing a nitrogen atom. As the monovalent organic group containing a nitrogen atom, monovalent organic groups containing at least one aromatic ring are preferred, and monovalent organic groups containing an aromatic ring and a =N—C(=S)— group are more preferred. $R^{16}$ and $R^{18}$ each may be the same or different, but are preferably the same for the reasons such as ease of production.

Examples of the compound (III) include 1,2-bis(dibenzylthiocarbamoyldithio)ethane, 1,3-bis(dibenzylthiocarbamoyldithio)propane, 1,4-bis(dibenzylthiocarbamoyldithio)butane, 1,5-bis(dibenzylthiocarbamoyldithio)pentane, 1,6-bis(dibenzylthiocarbamoyldithio)hexane, 1,7-bis(dibenzylthiocarbamoyldithio)heptane, 1,8-bis(dibenzylthiocarbamoyldithio)octane, 1,9-bis(dibenzylthiocarbamoyldithio)nonane, and 1,10-bis(dibenzylthiocarbamoyldithio)decane. Among these, 1,6-bis(dibenzylthiocarbamoyldithio)hexane is preferred because of being thermally stable and excellent in dispersibility into a rubber component.

Examples of a commercially available product of the compound (III) include VULCUREN TRIAL PRODUCT KA9188 and VULCUREN VPKA9188 (1,6-bis(dibenzylthiocarbamoyldithio)hexane) manufactured by Bayer AG.

In the present invention, organic compounds such as resorcinol, and resins such as resorcinol resins, modified resorcinol resins, cresol resins, modified cresol resins, phenol resins, and modified phenol resins may be used. Use of resorcinol or a resin thereof can improve the elongation at break and complex modulus of the vulcanized rubber composition. When the rubber composition is used for producing a rubber product to be in contact with a cord, use of resorcinol or a resin can improve the adhesive property with the cord.

Examples of resorcinol include resorcinol manufactured by SUMITOMO CHEMICAL COMPANY, LIMITED and the like. Examples of the resorcinol resin include resorcinol-formaldehyde condensates. Examples of the modified resorcinol resin include resorcinol resins in which repeating units are partially alkylated. Specific examples thereof include Penacolite resins B-18-S and B-20 manufactured by INDSPEC Chemical Corporation, SUMIKANOL 620 manufactured by Taoka Chemical Co., Ltd., R-6 manufactured by Uniroyal Chemical Co., SRF1501 manufactured by Schenectady Chemicals Inc., and Arofene 7209 manufactured by Ashland Inc.

Examples of the cresol resin include cresol-formaldehyde condensates. Examples of the modified cresol resin include cresol resins in which a methyl group at an end thereof is modified with a hydroxyl group and cresol resins in which repeating units are partially alkylated. Specific examples thereof include SUMIKANOL 610 manufactured by Taoka Chemical Co., Ltd. and PR-X11061 manufactured by Sumitomo Bakelite Co., Ltd.

Examples of the phenol resin include phenol·formaldehyde condensates. Examples of the modified phenol resin include resins obtained by modifying a phenol resin with cashew oil, tall oil, linseed oil, various vegetable oils, unsaturated fatty acids, rosin, alkylbenzene resins, aniline, melamine, or the like.

Examples of other resins include methoxylated methylolmelamine resins such as "SUMIKANOL 507AP" manufactured by SUMITOMO CHEMICAL COMPANY, LIMITED; coumarone-indene resins such as Coumarone resin NG4 manufactured by Nittetsu Chemical Industrial Co., Ltd. (softening point: 81 to 100° C.) and "Process Resin AC5" manufactured by Kobe Oil Chemical Industrial Co., Ltd. (softening point: 75° C.); terpene-based resins such as terpene resins, terpene-phenol resins, and aromatic modified terpene resins; rosin derivatives such as "NIKANOL® A70" manufactured by Mitsubishi Gas Chemical Company, Inc. (softening point: 70 to 90° C.); hydrogenated rosin derivatives; novolac-type alkylphenol resins; resol-type alkylphenol resins; C5-based petroleum resin; and liquid polybutadiene.

Examples of the viscoelasticity improving agent include N,N'-bis(2-methyl-2-nitropropyl)-1,6-hexanediamine (e.g., "SUMIFINE® 1162" manufactured by SUMITOMO CHEMICAL COMPANY, LIMITED), dithiouracil compounds described in Japanese Patent Laid-Open No. 63-23942, "TACKIROL® AP" and "TACKIROL® V-200" manufactured by Taoka Chemical Co., Ltd., alkylphenolsulfur chloride condensate described in Japanese Patent Laid-Open No. 2009-138148, 1,6-bis(dibenzylthiocarbamoyldithio)hexane (e.g., "KA9188" manufactured by Bayer AG), 1,6-hexamethylene dithiosulfate disodium salt dihydrate, 1,3-bis(citraconimide methyl)benzene (e.g., "Perkalink 900" manufactured by Flexsys), 1-benzoyl-2-phenyl hydrazide, carboxylic acid hydrazide derivatives such as 1-hydroxy-N'-(1-methylethylidene)-2-naphthoic acid hydrazide, 3-hydroxy-N'-(1-methylethylidene)-2-naphthoic acid hydrazide, 1-hydroxy-N'-(1-methylpropylidene)-2-naphthoic acid hydrazide described in Japanese Patent Laid-Open No. 2004-91505, 3-hydroxy-N'-(1-methylpropylidene)-2-naphthoic acid hydrazide, 1-hydroxy-N'-(1,3-dimethylbutylidene)-2-naphthoic acid hydrazide, 3-hydroxy-N'-(1,3-dimethylbutylidene)-2-naphthoic acid hydrazide, 1-hydroxy-N'-(2-furylmethylene)-2-naphthoic acid hydrazide, 3-hydroxy-N'-(2-furylmethylene)-2-naphthoic acid hydrazide, 3-hydroxy-N'-(1,3-dimethylbutylidene)-2-naphthoic acid hydrazide described in Japanese Patent Laid-Open No. 2000-190704, 3-hydroxy-N'-(1,3-diphenylethylidene)-2-naphthoic acid hydrazide, 3-hydroxy-N'-(1-methylethylidene)-2-naphthoic acid hydrazide, bismercaptooxadiazole compounds described in Japanese Patent Laid-Open No. 2006-328310, pyrithione salt compounds described in Japanese Patent Laid-Open No. 2009-40898, and cobalt hydroxide compounds described in Japanese Patent Laid-Open No. 2006-249361.

Examples of the anti-aging agent include those described on pages 436 to 443 in Gomu Kogyo Binran (Rubber Industry Handbook), 4th edition edited by Society of Rubber Industry, Japan. As the anti-aging agent, N-phenyl-N'-1,3-dimethylbutyl-p-phenylenediamine (abbreviation "6PPD", for example, "Antigen® 6C" manufactured by SUMITOMO CHEMICAL COMPANY, LIMITED), a reaction product of aniline and acetone (abbreviation "TMDQ"), poly(2,2,4-trimethyl-1,2-)dihydroquinoline) (e.g., Antioxidant FR manufactured by MATSUBARA INDUSTRIES, INC.), synthetic waxes (paraffin wax and the like), and vegetable waxes are preferably used.

When an anti-aging agent is used, the amount of the anti-aging agent is preferably 0.01 to 15 parts by weight, more preferably 0.1 to 10 parts by weight, and further preferably 0.1 to 5 parts by weight per 100 parts by weight of the rubber component.

Examples of the processing aid include fatty acids such as ricinoleic acid, palmitic acid, stearic acid, and oleic acid, amides and esters thereof, and fatty acid metal salts such as zinc stearate, barium stearate, calcium stearate, and zinc laurate. Examples of commercially available products include "STRUKTOL A50P", "STRUKTOL A60", "STRUKTOL EF44", "STRUKTOL HT204", "STRUKTOL HT207", "STRUKTOL HT254", "STRUKTOL HT266", and "STRUKTOL WB16" manufactured by SCHILL & SEILACHER Gmbh. & CO.

When a processing aid is used, the amount of the processing aid is preferably 0.01 to 20 parts by weight, more preferably 0.1 to 15 parts by weight, and further preferably 0.1 to 10 parts by weight per 100 parts by weight of the rubber component.

When stearic acid is used as the processing aid, the amount of stearic acid is preferably 0.01 to 15 parts by weight, more preferably 0.1 to 10 parts by weight, and further preferably 0.1 to 5 parts by weight per 100 parts by weight of the rubber component.

Examples of the oil include process oils and vegetable oils and fats. Examples of the process oil include paraffin-based process oils, naphthene-based process oils, aromatic-based process oils, MES (mild extracted solvate) oils, and TDAE (treated distilled aromatic extract) oils. Examples of commercially available products include aromatic oils ("NC-140" manufactured by Cosmo Oil Co., Ltd.), process oils ("Diana Process PS32" manufactured by Idemitsu Kosan Co., Ltd.), and TDAE oils ("VivaTec 500" manufactured by H&R Group).

When an oil is used, the amount of the oil is preferably 5 to 70 part by weight and more preferably 20 to 60 parts by weight per 100 parts by weight of the rubber component.

Examples of the wax include "SUNNOC® wax" manufactured by Ouchi Shinko Chemical Industrial Co., Ltd. and "OZOACE-0355" manufactured by Nippon Seiro Co., Ltd.

A peptizing agent is not particularly limited as long as it is usually used in the field of rubber. Examples thereof include aromatic mercaptan-based peptizing agents, aromatic disulfide-based peptizing agents, and aromatic mercaptan metal salt-based peptizing agents described on pages 446 to 449 in Gomu Kogyo Binran (Rubber Industry Handbook), 4th edition edited by Society of Rubber Industry, Japan. Among these, dixylyl disulfide and o,o'-dibenzamidodiphenyl disulfide ("NOCTIZER SS" manufactured by Ouchi Shinko Chemical Industrial Co., Ltd.) are preferred. One alone peptizing agent or two or more peptizing agents may be used either singly or as combined.

When a peptizing agent is used, the amount of the peptizing agent is preferably 0.01 to 1 part by weight and more preferably 0.05 to 0.5 parts by weight per 100 parts by weight of the rubber component.

Examples of the retarder include phthalic anhydride, benzoic acid, salicylic acid, N-nitrosodiphenylamine, N-(cyclohexylthio)phthalimide (CTP), sulfonamide derivatives, diphenylurea, bis(tridecyl)pentaerythritol diphosphite, and N-(cyclohexylthio)phthalimide (CTP) is preferably used.

When a retarder is used, the amount of the retarder is preferably 0.01 to 1 part by weight and more preferably 0.05 to 0.5 parts by weight per 100 parts by weight of the rubber component.

In the present invention, a compound having oxyethylene units having a structure represented by the formula: —O—(CH$_2$—CH$_2$—O)$_r$—H [wherein r is an integer of 1 or more.] may be used. Here, in the above formula, r is preferably 2 or more and more preferably 3 or more. r is preferably 16 or less and more preferably 14 or less. When r is 17 or more, compatibility with a rubber component and reinforcing performance tend to decrease.

The position of the oxyethylene unit in a compound having oxyethylene units may be in the main chain, terminal, or side chain. From the viewpoint of the sustainability of the effect of preventing static electricity accumulation and reduction of electrical resistance on the surface of the resulting tire, among the compounds having oxyethylene units, a compound having oxyethylene units at least in the side chain is preferable.

Examples of a compound having oxyethylene units in the main chain include polyoxyethylene alkyl ethers, polyoxyethylene alkyl phenyl ethers, monoethylene glycol, diethylene glycol, triethylene glycol, polyoxyethylene sorbitan fatty acid esters, polyoxyethylene polyoxypropylene alkyl ethers, polyoxyethylene alkylamines, polyoxyethylene styrenated alkyl ethers, and polyoxyethylene alkylamides.

When a compound having oxyethylene units at least in the side chain is used, the number of oxyethylene units is preferably 4 or more, and more preferably 8 or more, per 100 carbon atoms constituting the main chain. When the number of oxyethylene units is 3 or less, the electrical resistance tends to increase. The number of oxyethylene units is preferably 12 or less and more preferably 10 or less. When the number of oxyethylene units is 13 or more, compatibility with a rubber component and reinforcing performance tend to decrease.

When a compound having oxyethylene units at least in the side chain is used, the main chain thereof is preferably mainly constituted of polyethylene, polypropylene or polystyrene.

<Production of Rubber Composition>

The rubber composition of the present invention may be produced by kneading a rubber component, a vulcanization accelerator, silica, a compound (II), and as required, other components.

The rubber composition obtained by kneading additionally a sulfur component of the present invention (hereinafter, may be described as the "rubber composition containing a sulfur component of the present invention") may be produced by kneading a rubber component, a vulcanization accelerator, silica, a compound (II), a sulfur component, and as required, other components. The rubber composition containing a sulfur component of the present invention is preferably produced via, first, a step of kneading a rubber component, a filler such as silica, and as required, other components (hereinafter, may be abbreviated as "step 1"), and next, a step of kneading the rubber composition obtained in the step 1, a sulfur component, and as required, other components (hereinafter, may be abbreviated as "step 2"). A pre-kneading step for masticating the rubber component may be further included before the step 1 (i.e., kneading a rubber component and a filler and the like) to facilitate processing of the rubber component.

In the production of a rubber composition containing a sulfur component of the present invention, the total amount of the compound (II) may be kneaded with a rubber component and the like in any of the pre-kneading step, step 1, and step 2, or the compound (II) may be divided and kneaded with a rubber component and the like in at least two steps of the pre-kneading step to step 2. Alternatively, the compound (II) may be supported on the aforementioned filler in advance and then kneaded with a rubber component and the like.

When zinc oxide is blended, zinc oxide is preferably kneaded with a rubber component and the like in step 1. When stearic acid is blended, stearic acid is preferably kneaded with a rubber component and the like in step 1. When a vulcanization accelerator is blended, the vulcanization accelerator is preferably kneaded with a rubber component and the like in step 2. When a peptizing agent is blended, the peptizing agent is preferably kneaded with a rubber component and the like in step 1. When a pre-kneading step is included, it is preferable to knead the total amount of the peptizing agent with a rubber component in the pre-kneading step or divide the peptizing agent and knead a part thereof with the rubber component in both the pre-kneading step and step 1. When a retarder is blended the retarder is preferably kneaded with a rubber component and the like in step 2.

For kneading in the step 1, for example, an internal mixer including a Banbury mixer, an open kneader, a pressure kneader, an extruder, an injection molding apparatus and the like can be used. The temperature of the rubber composition at the end of kneading in the step 1 is preferably 200° C. or less and more preferably 120 to 180° C.

For kneading in the step 2, for example, an open roll, a calendar, and the like can be used. The kneading temperature (temperature of the rubber composition being kneaded) in the step 2 is preferably 60 to 120° C.

<Production of Vulcanized Rubber Composition>

Vulcanization of the rubber composition containing a sulfur component of the present invention enables a vulcanized rubber composition to be produced. A vulcanized rubber composition may be produced by processing the rubber composition containing a sulfur component of the present invention into a particular shape and then vulcanizing the rubber composition.

The vulcanizing temperature is preferably 120 to 180° C. Those skilled in the art can appropriately determine the vulcanizing time according to the composition of the rubber composition. Vulcanization is generally performed under normal pressure or under pressure.

<Application>

The rubber composition and vulcanized rubber composition of the present invention are useful for producing various products (e.g., tires, tire members, vibration-proof rubber, conveyor belt rubber, and engine mount rubber). As such products, tires and tire members are preferred, and tires are more preferred. Examples of the tire member include a tire belt member containing a vulcanized rubber composition of the present invention and a steel cord, a tire carcass member containing a vulcanized rubber composition of the present invention and a carcass fiber cord, a tire side wall member, a tire inner liner member, a tire cap tread member, and a tire under tread member.

EXAMPLES

While the present invention is more specifically described in the following by referring to Examples, the present invention is not limited by the following Examples. The present invention can be implemented by appropriately adding changes within the range compatible to the gist described above and below, and they are all included in the technical scope of the present invention.

Production Example 1: Production of Compound (Ia-1) (1,3-bis(4,6-dimethylpyrimidin-2-yl)trisulfide)

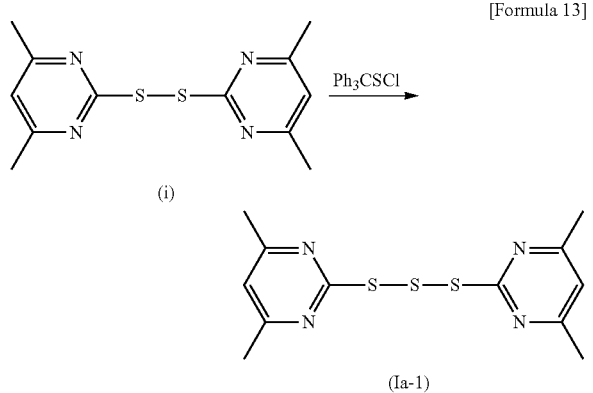

Under a nitrogen atmosphere, a compound (i) (1,2-bis(4,6-dimethylpyrimidin-2-yl)disulfide) (186 g, 668 mmol), triphenylmethanesulfenyl chloride (manufactured by Tokyo Chemical Industry Co., Ltd.) (208 g, 669 mmol), and 668 mL of chloroform were mixed. A reaction was conducted by refluxing the resulting mixture with heating for 3 hours. After the reaction was finished, the mixture was left to cool, and 500 mL of water was added to the mixture. After an hour of stirring, the mixture was separated into an aqueous layer and an organic layer. The aqueous layer was extracted with 300 mL of chloroform to thereby separate the aqueous layer into an aqueous layer and an organic layer. The organic layers were combined and washed with 200 mL of brine. The washed organic layer was dried over sodium sulfate and then subjected to filtration. The resulting filtrate was concentrated under reduced pressure to obtain a crude product. The resulting crude product was purified with silica gel column chromatography (developing solvent (dichloromethane/ethyl acetate=100/0 to 2/1 (volume ratio))) to obtain 7.7 g of a compound (Ia-1).

$^1$H-NMR of compound (Ia-1) (CDCl$_3$, 400 MHz) δ (ppm): 2.47 (12H, s), 6.82 (2H, s)

Example 1

Step 1

Using a Labo Plastomill (manufactured by Toyo Seiki Seisaku-sho, Ltd., capacity: 600 mL), 80 parts by weight of a styrene-butadiene copolymer rubber ("SBR TUFDENE 2000" manufactured by Asahi Kasei Corporation), 20 parts by weight of a butadiene rubber ("BR01" manufactured by JSR Corporation), 75 parts by weight of silica ("Nipsil® AQ" manufactured by Tosoh Silica Corporation, BET specific surface area: 205 m$^2$/g), 5 parts by weight of carbon black HAF ("Asahi #70" manufactured by Asahi Carbon Co., Ltd.), 2 parts by weight of stearic acid, 3 parts by weight of zinc oxide, 1.5 parts by weight of "Antigen® 6C" manufactured by SUMITOMO CHEMICAL COMPANY, LIMITED, 30 parts by weight of a TDAE oil ("VivaTec 500" manufactured by H&R Group), and 6 parts by weight of a compound that can be bonded to silica ("Si-75" manufactured by Evonik Industries AG), and 0.5 parts by weight of a compound (Ia-1) were kneaded to obtain a rubber composition. In the step, all the components described above were placed in a Labo Plastomill that was set at a temperature of 140° C. and rotated at a rotor rotation speed of 25 rpm. Then, the mixture in the Labo Plastomill was kneaded at a rotor rotation speed of 50 rpm for 3.5 minutes and further at a rotor rotation speed of 80 rpm for 1.5 minutes. The temperature of the rubber composition at the completion of kneading was 155 to 165° C.

Step 2

The rubber composition obtained in the step 1, a vulcanization accelerator (1.4 parts by weight of N-cyclohexyl-2-benzothiazolylsulfenamide (CBS) and 2.0 parts by weight of diphenylguanidine (DPG)), and 1.8 parts by weight of a powder sulfur ("Fine powder sulfur" manufactured by Hosoi Chemical Industry Co., Ltd.) were kneaded in an open roll machine at a roll setting temperature of 60° C. to obtain a rubber composition.

<Vulcanization>

The rubber composition obtained in the step 2 was heated at 170° C. for 15 minutes to thereby obtain a vulcanized rubber composition.

Examples 2 to 3 and Comparative Example 1

In the same manner as in Example 1 except that components in the kind and amount shown in Table 1 were used in the steps 1 and 2 to obtain vulcanized rubber compositions of Examples 2 to 3 and Comparative Example 1.

The styrene-butadiene copolymer rubber and the like used were the same as those in Example 1.

For evaluation of the abrasion resistance mentioned below, the amounts of the powder sulfur, CBS, and DPG were adjusted in Examples 1 to 3 such that the hardness of the vulcanized rubber compositions of Examples 1 to 3 was equivalent to the hardness of the vulcanized rubber composition of Comparative Example 1.

<Evaluation of Abrasion Resistance>

A DIN abrasion tester AB-6111 (manufactured by Ueshima Seisakusho Co., Ltd.) was used to measure the abrasion volume (unit: mm$^3$) of the vulcanized rubber composition of each of Examples 1 to 3, in each of which the compound (Ia-1) was used, and the vulcanized rubber composition of Comparative Example 1, in which the compound (Ia-1) was not used, in accordance with JIS K6264-2:2005 "Rubber, vulcanized or thermoplastic-Determination of abrasion resistance". The index of abrasion resistance of the vulcanized rubber composition of each of Examples 1 to 3 was calculated by the following expression:

Index of abrasion resistance=100×(abrasion volume of Comparative Example 1)/(abrasion volume of each of Examples 1 to 3).

The results are shown in Table 1. As this index is the larger, the abrasion resistance is the better.

TABLE 1

|  |  | Example 1 | Example 2 | Example 3 | Comparative Example 1 |
|---|---|---|---|---|---|
| Step 1 | Styrene-butadiene copolymer rubber (parts) | 80 | 80 | 80 | 80 |
|  | Butadiene rubber (parts) | 20 | 20 | 20 | 20 |
|  | Silica (parts) | 75 | 75 | 75 | 75 |
|  | Carbon black (parts) | 5 | 5 | 5 | 5 |
|  | Stearic acid (parts) | 2 | 2 | 2 | 2 |
|  | Zinc oxide (parts) | 3 | 3 | 3 | 3 |
|  | Anti-aging agent (parts) | 1.5 | 1.5 | 1.5 | 1.5 |
|  | Compound (Ia-1) (parts) | 0.5 | 1 | 2 | — |
|  | TDAE oil (parts) | 30 | 30 | 30 | 30 |
|  | Compound that can be bonded to silica (parts) | 6 | 6 | 6 | 6 |
| Step 2 | Powder sulfur (parts) | 1.8 | 1.6 | 1.2 | 2 |
|  | CBS (parts) | 1.4 | 1.2 | 0.9 | 1.5 |
|  | DPG (parts) | 2 | 2 | 2 | 2 |
| Evaluation | Index of abrasion resistance | 122 | 136 | 190 | — |

(Note)
parts = parts by weight,
% = % by weight

As shown in Table 1, use of the compound (Ia-1) can improve the abrasion resistance of the vulcanized rubber composition.

INDUSTRIAL APPLICABILITY

The compound of the present invention is useful for improving the abrasion resistance of the vulcanized rubber composition.

The present application is based on Japanese Patent Application No. 2019-107337 filed in Japan, the entire contents of which are incorporated in the present description.

The invention claimed is:

1. A rubber composition obtained by kneading a rubber component, a vulcanization accelerator, silica, and a compound represented by the formula (II):

[Formula 2]

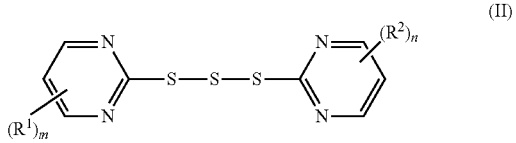

wherein,
m and n each independently represent an integer of 1 to 3, and
$R^1$ and $R^2$ each independently represent a halogen atom, a $C_{1-18}$ alkyl group optionally having a substituent, a $C_{3-10}$ cycloalkyl group optionally having a substituent, a $C_{6-18}$ aryl group optionally having a substituent, a $C_{7-20}$ aralkyl group optionally having a substituent, a carboxy group, a $C_{1-18}$ alkoxy-carbonyl group optionally having a substituent, a $C_{3-10}$ cycloalkyloxy-carbonyl group optionally having a substituent, a $C_{6-18}$ aryloxy-carbonyl group optionally having a substituent, a $C_{7-20}$ aralkyloxy-carbonyl group optionally having a substituent, a carbamoyl group optionally having a substituent, a hydroxy group, a $C_{1-18}$ alkoxy group optionally having a substituent, a $C_{3-10}$ cycloalkyloxy group optionally having a substituent, a $C_{6-18}$ aryloxy group optionally having a substituent, a $C_{7-20}$ aralkyloxy group optionally having a substituent, a $C_{1-18}$ alkyl-carbonyloxy group optionally having a substituent, a $C_{3-10}$ cycloalkyl-carbonyloxy group optionally having a substituent, a $C_{6-18}$ aryl-carbonyloxy group optionally having a substituent, a $C_{7-20}$ aralkyl-carbonyloxy group optionally having a substituent, an amino group optionally having a substituent, or a nitro group, when m is 2 or 3, a plurality of $R^1$'s each may be the same or different, and when n is 2 or 3, a plurality of $R^2$'s each may be the same or different.

2. The rubber composition according to claim 1, wherein $R^1$ and $R^2$ are each independently a $C_{1-18}$ alkyl group optionally having a substituent, a hydroxy group, a $C_{1-18}$ alkoxy group optionally having a substituent, a $C_{1-18}$ alkyl-carbonyloxy group optionally having a substituent, an amino group, or a mono($C_{1-18}$ alkyl-carbonyl)amino group (the $C_{1-18}$ alkyl optionally has a substituent), when m is 2 or 3, a plurality of $R^1$'s each may be the same or different, and when n is 2 or 3, a plurality of $R^2$'s each may be the same or different.

3. The rubber composition according to claim 1, wherein $R^1$ and $R^2$ are each independently a $C_{1-6}$ alkyl group, when m is 2 or 3, a plurality of $R^1$'s each may be the same or different, and when n is 2 or 3, a plurality of $R^2$'s each may be the same or different.

4. The rubber composition according to claim 1, wherein m and n are each independently an integer of 1 to 3.

5. The rubber composition according to claim 1, wherein both m and n are 2.

6. The rubber composition according to claim 1, wherein the rubber component contains a diene-based rubber.

7. The rubber composition according to claim 1, wherein the rubber component contains a styrene-butadiene copolymer rubber.

8. The rubber composition according to claim 1 obtained by kneading additionally carbon black.

9. The rubber composition according to claim 1 obtained by kneading additionally a sulfur component.

10. A vulcanized rubber composition obtained by vulcanizing the rubber composition according to claim 9.

11. A tire comprising the vulcanized rubber composition according to claim 10.

* * * * *